United States Patent [19]

Yodoi et al.

[11] Patent Number: 5,210,073
[45] Date of Patent: May 11, 1993

[54] METHOD FOR TREATING CANCER THERAPY RADIATION DAMAGE OR ARTERIOSCLEROSIS USING HUMAN ADF

[75] Inventors: Junji Yodoi, Kitashirakawa Nishisenouchi-cho 39, Kyoto-fu, Kyoto-shi, Sakyo-ku; Atsushi Uchida, Uji; Yutaka Tagaya, Kobe; Akira Mitsui; Tadashi Hirakawa, both of Kawasaki, all of Japan

[73] Assignees: Ajinomoto Co., Inc., Tokyo; Junji Yodoi, Kyoto, both of Japan

[21] Appl. No.: 589,616

[22] Filed: Sep. 28, 1990

[30] Foreign Application Priority Data

Sep. 29, 1989 [JP] Japan .................................. 1-256369

[51] Int. Cl.$^5$ ...................... C07K 13/00; A61K 37/02
[52] U.S. Cl. ........................ 514/12; 514/824; 514/917; 514/886; 514/2; 514/21
[58] Field of Search ................... 514/12, 21, 2

[56] References Cited

FOREIGN PATENT DOCUMENTS 237189 9/1987 European Pat. Off. .
299206 1/1989 European Pat. Off. .

OTHER PUBLICATIONS

Biochemical and Biophysical Research Communications, vol. 163, No. 3, Sep. 29, 1989, pp. 1466-1472, Duluth, US; M. Kuzuya et al.: "Protective role of intracellular glutathione against oxidized low density lipoprotein in cultured endothelial cells" pp. 1466-1467, paragraph: Introduction; p. 1468, FIG. 3; pp. 1471-1472, paragraph: Discussion*.

Rheumatol, Int., vol. 4, 1984, pp. 35-38, Berlin, DE; N. D. Hall et al.: "The oxidation of serum sulph-hydryl groups by hydrogen peroxide secreted by stimulated phagocytic cells in rheumatoid arthritis" *pp. 37-38, paragraph: Discussion.

Biochemical and Biophysical Research Communications, vol. 136, No. 2, Apr. 29, 1986, pp. 630-637, Duluth, US; K. U. Schallreuter et al.: "The role of thioredoxin reductase in the reduction of free radicals at the surface of the epidermis" *p. 630, paragraph: Introduction pp. 634-636, par.: Discussion.

Experientia, vol. 45, Jan. 1989, pp. 41-52, Basel, CH; A. Rojas et al.: "Modifiers of readiosensitivity" *p. 42, column 1; pp. 46-50*.

Primary Examiner—Garnette D. Draper
Assistant Examiner—Shelly J. Guest
Attorney, Agent, or Firm—Oblon, Spivak, McClelland, Maier & Neustadt

[57] ABSTRACT

A composition and method for the treatment of inflammation, rheumatism, autoimmune disease, ischemic damage of organs, drug toxicity and arteriosclerosis comprising human ADF is disclosed.

5 Claims, 4 Drawing Sheets (N-TERMINAL) Val-Lys-Gln-Ile-Glu-Ser-Lys-Thr-Ala-Phe-Gln-
Glu-Ala-Leu-Asp-Ala-Ala-Gly-Asp-Lys-Leu-Val-
Val-Val-Asp-Phe-Ser-Ala-Thr-Trp-Cys-Gly-Pro-
Cys-Lys-Met-Ile-Lys-Pro-Phe-Phe-His-Ser-Leu-
50
Ser-Glu-Lys-Tyr-Ser-Asn-Val-Ile-Phe-Leu-Glu-
Val-Asp-Val-Asp-Asp-Cys-Gln-Asp-Val-Ala-Ser-
Glu-Cys-Glu-Val-Lys-Cys-Met-Pro-Thr-Phe-Gln-
Phe-Phe-Lys-Lys-Gly-Gln-Lys-Val-Gly-Glu-Phe-
Ser-Gly-Ala-Asn-Lys-Glu-Lys-Leu-Glu-Ala-Thr-
100
Ile-Asn-Glu-Leu-Val (C-TERMINAL)

*FIG. 1*

METHOD FOR TREATING CANCER THERAPY RADIATION DAMAGE OR ARTERIOSCLEROSIS USING HUMAN ADF

BACKGROUND OF THE INVENTION

1. Field of the Invention

The present invention relates to a radioprotective composition, an antiinflammatory composition, a composition for the treatment of rheumatism, a composition for the treatment of autoimmune disease, a composition for the treatment of ischemic damage of organs, a composition for the treatment of drug toxicity and a composition for the treatment of arteriosclerosis, comprising as an effective ingredient human adult T cell leukemia-derived factor (hereafter referred to as human ADF).

2. Description of the Background

Radiation is an effective cancer therapy however, radiation non-specifically destroys not only cancer cells but also normal cells. Therefore, as the dose of radiation is increased for the purpose of enhancing its therapeutic effect, side effects such as erythropoietic disorders, pyrexia and vomiting are unavoidable. Furthermore, even if the cancer is cured, complications such as developmental anomalies due to abnormalities in internal secretions and disorders in the central nervous system can develop.

In actual therapy, attention has been paid only to tumor regression effect. However, as therapeutic results are improved and life span increases, it has become essential to ensure "quality of life" of pre- and post-operative patients. Thus it is important to minimize the disturbance of normal cells as much as possible and to alleviate side effects by using radiation-protective agents in combination with radiotherapy to enhance the therapeutic results.

Cytotoxicity due to radiation is considered to be caused by free radicals which are produced by radiation in living bodies. Reducing glutathione (GSH) and other thiol (SH) compounds have been investigated and developed as radiation-protective agents based on the concept of inactivating the free radicals produced by radiation. However, GSH has been found to be effective only in vitro. Since it could not permeate through the cell membrane, the effect of GSH was hardly noted when it was administered to an animal.

The compound, WR-2721 (S-2-(3-aminopropyl-amino)-ethylphosphorothioic acid), which was one of the SH compounds developed in the United States of America, could prevent disorders of bone marrow stem cells caused by radiation but WR-2721 has a serious side effect, and its manufacture was discontinued in Japan.

It has been found that interleukin 1 (IL1), which is a protein derived from the living body, also has a radiation protecting activity. However, IL1 is pyretic and its dose is thus limited when IL1 is administered to humans. In addition its mechanism is not exactly known, so that it is difficult to freely control its activity. Therefore, no protecting agent that can effectively prevent side effects in radiotherapy and also has low toxicity exists in the prior art.

Free radicals are considered to be a cause of injury to the body due to radiation and are also generated in the body in large quantities in inflammation, rheumatism, autoimmune disease, ischemic damages of organs, drug toxicity, etc. It is believed that free radicals attack plasma membranes, proteins, enzymes and DNA through their potent oxidation (peroxidation) activity.

Arteriosclerosis is also thought to be caused by the accumulation of lipid peroxide, which is a source of free radicals. Therefore, where SH compounds having a radioprotective activity have a strong free radical scavenging action, they can be effectively utilized as therapeutic or prophylactic agents against inflammation or the other various diseases described above which are associated with peroxidation in the body.

Superoxide dismutase (SOD) has an activity of scavenging $O_2^-$ which is a free radical. Investigations are now under way to develop SOD as an antiinflammatory agent. However, its half-life in the body is very short, within 10 minutes, so that it is necessary to make a device by chemical modification or containment in liposomes, etc., in order to prolong the half-life. Such requirements result in problems in clinical applications of SOD.

On the other hand, Wollman et al. published the amino acid sequence of thioredoxin which is an oxidation-reduction protein in the human body (The Journal of Biological Chemistry, Vol. 263 (No. 30), PP. 15506–15512, 1988). The amino acid sequence of thioredoxin shown by Wollman et al. has a similar sequence to that of human ADF but two amino acids are different.

Human ADF also has a thioredoxin-like oxidation-reduction activity. Accordingly, some researchers refer to human ADF as thioredoxin but in the present invention the term human ADF is consistently used.

The free radical scavenging activity of human ADF (human thioredoxin) having an oxidation-reduction ability has not been clarified until the present inventor has reported.

SUMMARY OF THE INVENTION

By the use of human ADF in accordance with the present invention, in combination with radiotherapy for cancer, etc., side effects caused by radiation can be greatly reduced. Furthermore, human ADF has an activity of neutralizing free radicals and hence can be widely utilized as an agent for the treatment or prevention of various diseases which are accompanied by tissue damage due to oxidation caused by free radicals in the living body such as inflammation, rheumatism, autoimmune disease, ischemic damages of organs, drug toxicity, arteriosclerosis, etc.

An object of the present invention is to provide pharmaceutical compositions comprising human ADF which can effectively reduce side effects caused by radiation in radiotherapy of cancer, etc., and furthermore can be effective for the treatment and prevention of (1) inflammation caused by free radicals or (2) various inflammation associated with peroxidation in the body, and which has low toxicity.

As a result of extensive investigations to solve the problems described above, the present inventor has found that human ADF has excellent radioprotective and antiinflammatory effects and excellent effects for treating rheumatism, autoimmune disease, ischemic damage of organs, drug toxicity and arteriosclerosis.

A more complete appreciation of the invention and many of the attendant advantages thereof will be readily obtained as the same becomes better understood by reference to the following detailed description when considered in connection with the accompanying drawings, wherein:

BRIEF DESCRIPTION OF THE DRAWINGS

FIG. 1 shows an amino acid sequence of human ADF.

DETAILED DESCRIPTION OF THE PREFERRED EMBODIMENTS

Figure 2:
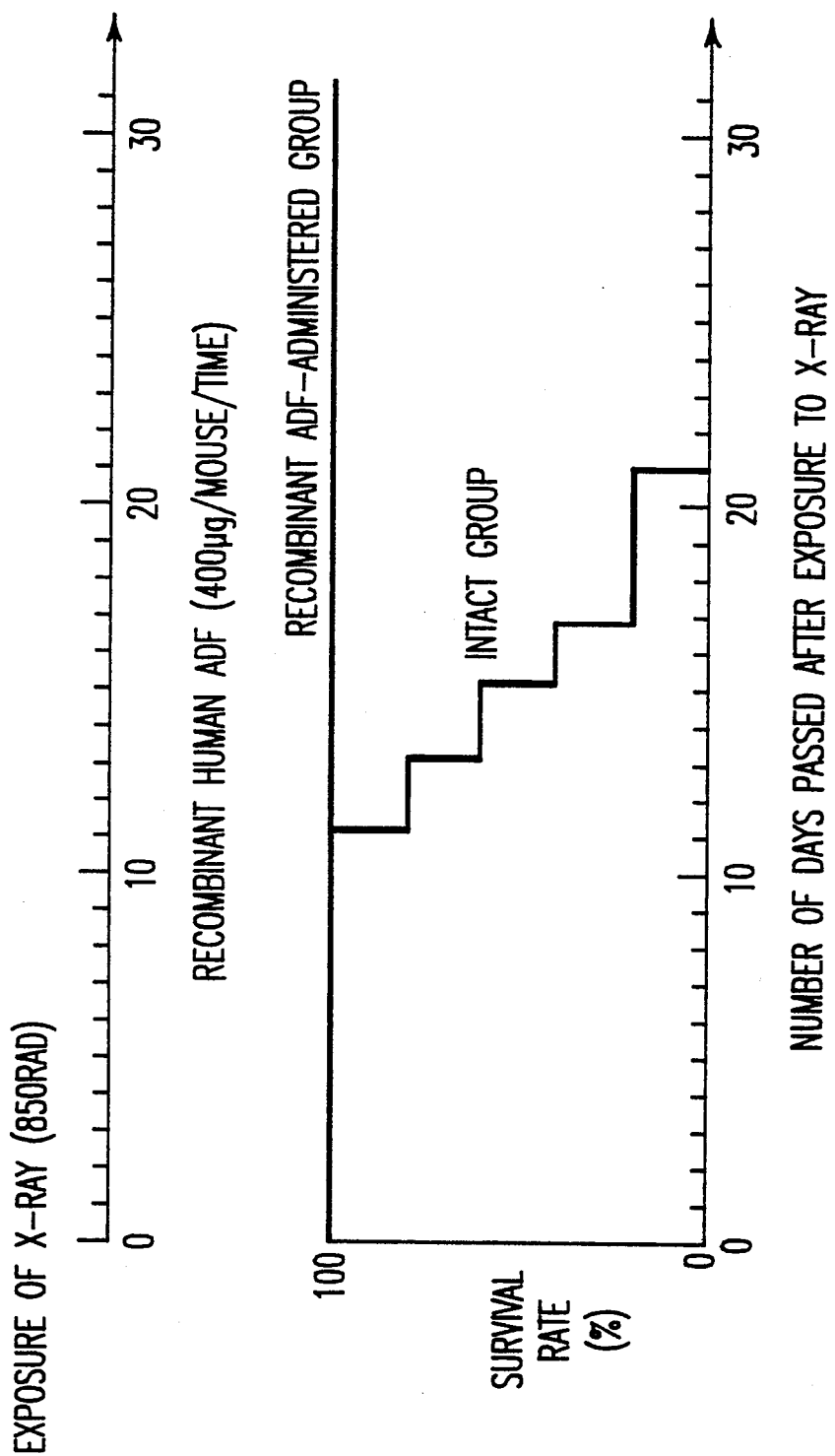
FIG. 2 shows a radioprotective effect of human ADF.

Human ADF is a human-derived protein and hence is not recognized as a foreign matter when administered to humans so that its toxicity is extremely low. In addition, since the half-life in blood is as long as 1.5 hour, and is longer by more than 10 times that of SOD, human ADF exhibits its effects in a much lower concentration than SOD.

Human ADF is a protein first found in the culture supernatant of T cell leukemia cell line (ATL-2) established from human adult T cell leukemia. The present inventor has already succeeded in the purification of the protein and cloning of cDNA and has succeeded in mass production of recombinant human ADF by genetic recombination (Japanese Patent Application Laid-Open No. 85097/1989; U.S. application No. 07/201,201). Human ADF has an active site structure common to thioredoxin redox protein derived from *Escherichia coli*, higher plants, rabbits, etc. In addition, it has also been confirmed that recombinant human ADF has a thioredoxin-like reducing activity.

As the human ADF protein used in the present invention, any protein prepared by the following method or any other method is usable as long as that protein has the thioredoxin-like reducing activity. Therefore, the method of producing ADF is not limited.

(1) Human ADF protein is purified from the culture supernatant of cells or cell extracts of a human-derived cell line (ATL-2, etc.) in a conventional manner such as salting out, gel filtration chromatography, ion exchange chromatography, affinity chromatography, chromatofocusing, reverse phase chromatography, hydrophobic chromatography, etc. (Japanese Patent Application Laid-Open No. 85097/1989).

(2) By genetic recombination techniques, cDNA or genome DNA of human ADF is transduced into host cells such as *Escherichia coli*, *Bacillus subtilis*, yeast, higher animal cells, plant cells, etc., and recombinant human ADF protein expressed in the host cells is purified by means as described in (1) (Japanese Patent Application Laid-open No. 85097/1989).

(3) By chemical peptide synthesis, the polypeptide having the sequence of (I) can be synthesized.

Any of the methods described above may be used.

By administering the human ADF composition of the present invention upon radiotherapy, side effects caused by radiation can be greatly reduced. For example, the human ADF of the present invention can be applied to various diseases including various cancers requiring treatment of the total body or local irradiation with X-rays, and to diseases such as acute and chronic leukemia and aplastic anemia, which require total body irradiation with X-rays prior to transplantation of bone marrow. Furthermore, human ADF is a protein derived from the human so it is not recognized as a foreign matter when it is administered to the human body. Thus its toxicity is very low.

Human ADF is administered in a dose of 1 to 30 mg/kg body weight before or after or, alternatively, before and after irradiation, by dividing the dose into several portions. The time period for administration is desirably within one day immediately before or immediately after irradiation. A dose is preferably about 10 mg/kg body weight but may be varied depending upon the dose of radiation and condition of the patient. The route for administration may be intravenous administration, intramuscular administration or any other administration.

The human ADF of the present invention is also capable of reducing and scavenging various free radicals. In addition, when free radicals react with proteins or enzymes having S-S crosslinking, incorrect S-S linkages are formed intramolecularly or intermolecularly, causing them to loose their activity. The human ADF of the present invention also has the ability to correct the S-S crosslinking in the thus inactivated proteins or enzymes and thereby recover their activity. Therefore, conditions in inflammation accompaning injury of the body due to free radicals or diseases such as rheumatism, autoimmune disease, ischemic damage of organs and drug toxicity, chemical toxicity, etc. can be greatly alleviated by administering the human ADF. The human ADF can also be utilized as an agent for the prevention and treatment of arteriosclerosis which is considered to be caused by the accumulation of free radicals.

The human ADF used in the present invention is not limited to the polypeptide having the sequence shown in FIG. 1. Thus, a polypeptide with an added methionine residue at the N-terminal thereof, a polypeptide having an amino acid sequence with additional substitution by chemical modification or nucleotide substitution, a polypeptide having an amino acid sequence which is in part deficient, a polypeptide having an amino acid sequence with an insertion, or a polypeptide with added sugar chains at the side chain thereof may also be used, as long as they retain the human ADF activity. Preferred polypeptides are a polypeptide having the amino acid sequence shown in FIG. 1 and a polypeptide having a structure in which Met is added to the N-terminal of the amino acid sequence shown in FIG. 1. Furthermore, the active site of human ADF has already been revealed so that it is also possible to freely control its activity by means of protein engineering.

The content of human ADF in pharmaceutical compositions of the present invention is not particularly limited. The human ADF may be contained in a dose of 0.01 to 100.0 wt%, preferably 0.1 to 50 wt%. In addition to the human ADF, various physiologically acceptable stabilizers and excipients such as mannitol, maltose, etc. may be added.

Other features of the invention will become apparent in the course of the following descriptions of exemplary embodiments which are given for illustration of the invention and are not intended to be limiting thereof.

EXAMPLE 1

Preparation of recombinant human ADF

Following Japanese Patent Application Laid-Open No. 85097/1989, recombinant human ADF was prepared. Firstly, *Escherichia coli* was transformed with plasmid DNA into which human ADF cDNA had been incorporated, to express human ADF in *Escherichia coli*. Subsequent purification by ion exchange chromatography, etc., gave recombinant human ADF. From 20 liters of the culture of *Escherichia coli*, 1 g of the purified protein was obtained. The standard product showed a single band of molecular weight of 12,000 by SDS-PAGE. By immunoblotting, it reacted with anti-human ADF antibodies. The thus obtained human ADF had a thioredoxin-like reducing activity. Its specific activity was comparable to that of *Escherichia coli*-derived thioredoxin.

Recombinant human ADF was dialyzed to phosphate buffered saline (PBS) overnight, the dialysate was passed through a millipore filter of 0.22 μm to sterilize it. After adjusting its concentration to 0.5 mg/ml, the recombinant human ADF was used for the following experiment.

EXAMPLE 2

Radioprotective effect of recombinant human ADF in vivo

Immediately after (Day 0) irradiation of mice with 8.5 Gy X-rays (ICR, age of 9 weeks, male), recombinant human ADF was intraperitoneally administered every other day for 10 days by 6 times in total. The dose was 400 μg/mouse/time. As shown in FIG. 2, mice in the control group to which no human ADF was administered began to die on or after Day 11 from the irradiation and all mice died up to Day 21. On the contrary, all mice survived even on Day 30 in the recombinant human ADF-administered group.

EXAMPLE 3

Reducing activity of free radical by recombinant human ADF

Figure 3:
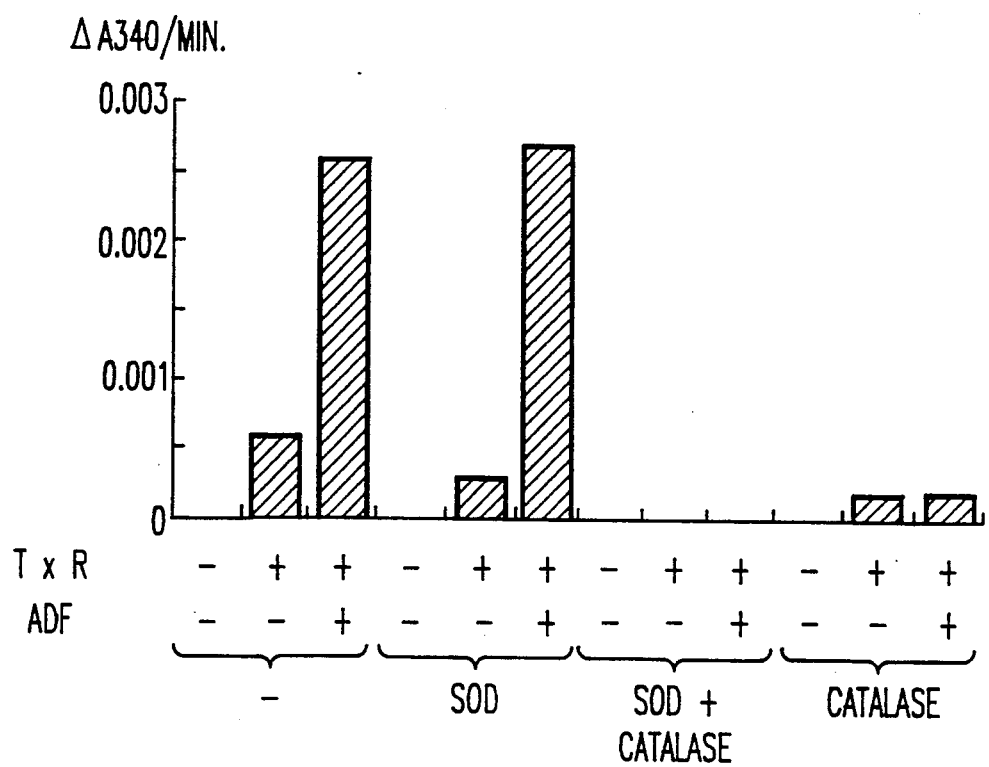
FIG. 3 shows reducing activity of free radical by human ADF.

It was revealed that the human ADF of the present invention had an activity of reducing free radicals. As shown in FIG. 3, the system of forming free radicals ($O_2-$, $H_2O_2$) consisting of xanthine oxidase and xanthine was added to the reduced thioredoxin reproduction system consisting of recombinant human ADF, thioredoxin reductase (TxR) and NADPH, whereby reduction in absorbance at 340nm associated with consumption of NADPH was observed. This reaction was hardly observed in the absence of ADF. Furthermore, this reaction was not inhibited by SOD which is a superoxide ($O_2^-$) scavenging enzyme but inhibited by catalase which is a hydrogen peroxide ($H_2O_2$) scavenging enzyme. It was thus revealed that the human ADF was capable of reducing hydrogen peroxide.

In FIG. 3, $\Delta A340$/min shows a decrease in absorbance at 340 nm.

EXAMPLE 4

Reactivation effect of inactivated enzyme by recombinant human ADF

Figure 4:
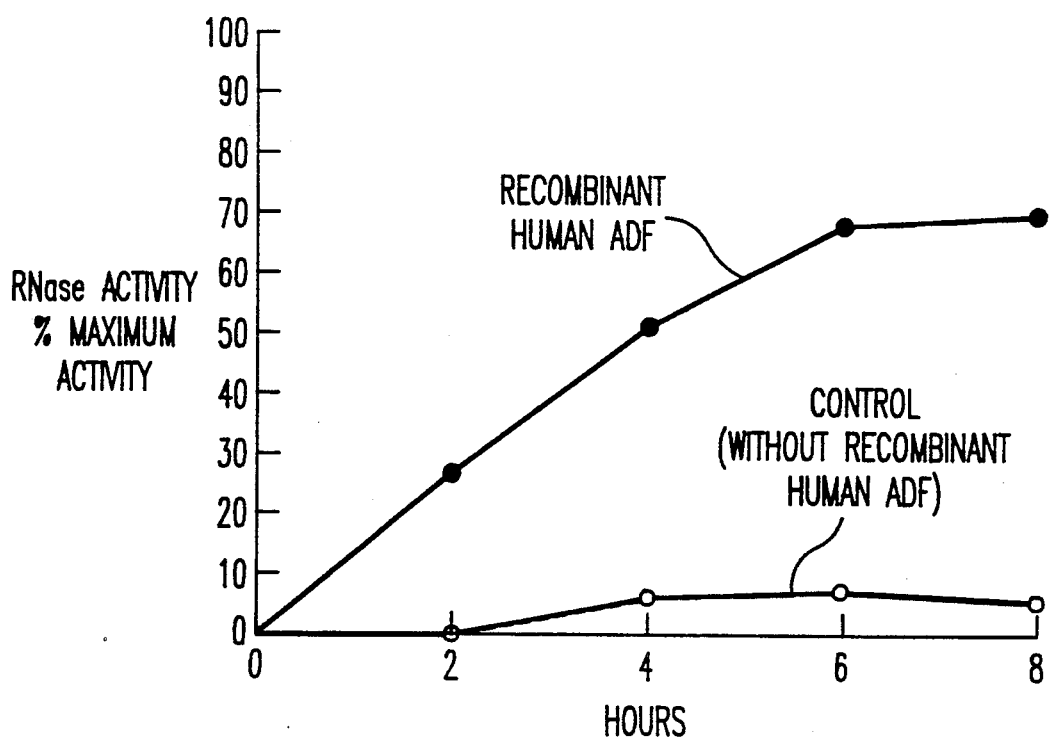
FIG. 4 shows reactivation effect of inactivated enzyme by human ADF.

It was revealed that the human ADF of the present invention has an activity of recovering the enzyme activity inactivated by free radicals (FIG. 4). Ribonuclease (RNase) possesses four S-S linkages. When the S-S linkages are reduced with a reducing agent, dithiothreitol (DTT), followed by reacting with hydrogen peroxide ($H_2O_2$), which is a source of free radicals, then incorrect S-S crosslinkages are formed intramolecularly or intermolecularly, with the result that scrambled RNase lacking activity is formed.

Figure 5:
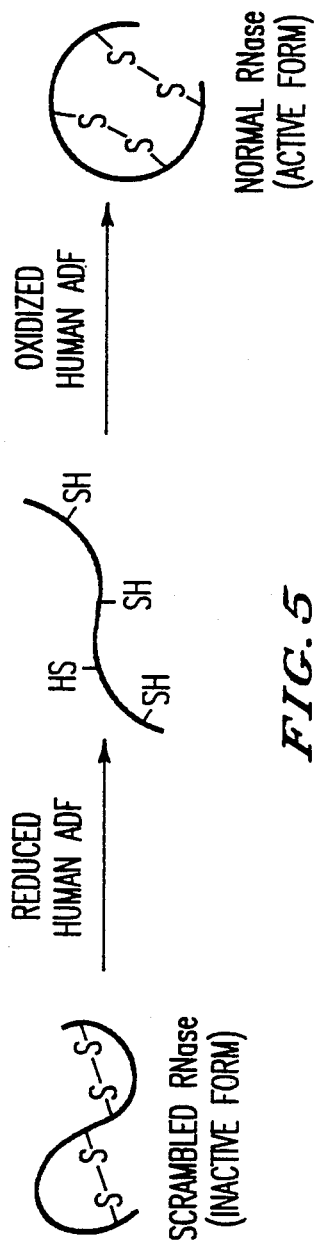
FIG. 5 shows structural change in RNase.

The scrambled RNase lost its activity, but when the oxidized and reduced recombinant human ADF was reacted at this stage, the activity of RNase was recovered with the passage of time. As shown in FIG. 5, this reaction is believed to occur because the incorrect S-S linkages are cleaved by the reduced ADF and the correct S-S linkages are then formed by the oxidized ADF. The RNase activity was determined by measuring a rate of increasing absorbance at 286 nm associated with the hydrolysis of 2',3'-cCMP. The results are shown in FIG. 4.

EXAMPLE 5

Kinetics of recombinant human ADF in blood

Figure 6:
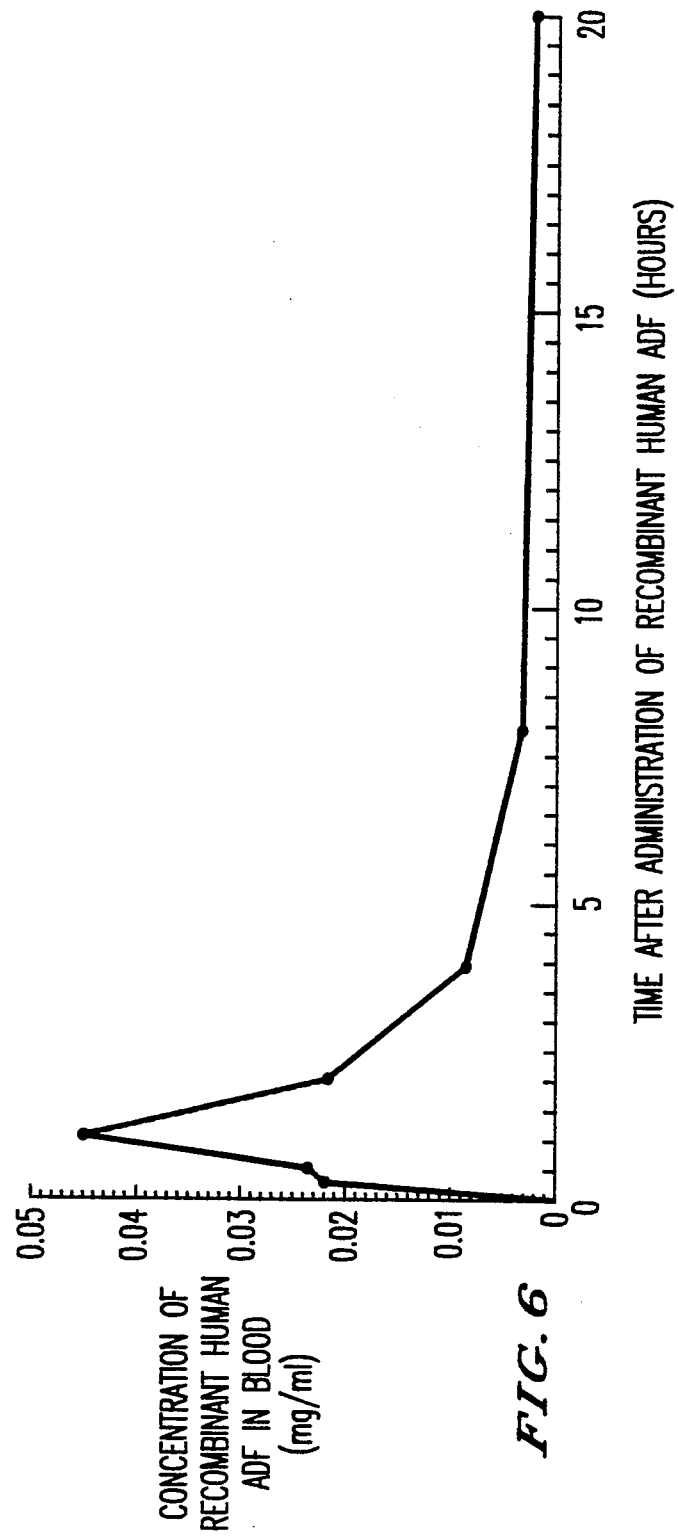
FIG. 6 shows kinetics of human ADF in blood.

After 2.5 mg (dissolved in 1 ml of physiological saline) of recombinant human ADF (hereafter simply referred to as rADF) was intraperitoneally administered to mouse (C57BL/6, age of 4 weeks, female), the mouse was anesthetized with ether after a definite period of time lapsed. Blood was then collected from the heart then the serum was collected. After rADF contained in the sera was detected by SDS-PAGE and immunoblotting, bands of rADF on the blotting membrane were quantitatively determined by densitometer to calculate the concentration of rADF in the serum. As shown in FIG. 6, rADF appeared in the blood at 15 minutes after the administration. The blood concentration reached the maximum at 1 hr. after administration and then gradually decreased. From these results, the half-life of rADF in blood was calculated to be about 1.5 hour and indicates that the half-life of rADF in blood is much longer than that of SOD.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for treating cancer therapy radiation damage or arteriosclerosis which comprises administering a therapeutically effective amount of human adult T cell leukemia-derived factor to an individual in need of treatment for cancer therapy radiation damage or arteriosclerosis.

2. The method of claim 1 wherein said human adult T cell leukemia-derived factor has the amino acid sequence beginning with the N-terminus:

1
Val—Lys—Gln—Ile—Glu—Ser—Lys—Thr—Ala—Phe—Gln—
Glu—Ala—Leu—Asp—Ala—Ala—Gly—Asp—Lys—Leu—Val—
Val—Val—Asp—Phe—Ser—Ala—Thr—Trp—Cys—Gly—Pro—
Cys—Lys—Met—Ile—Lys—Pro—Phe—Phe—His—Ser—Leu—
50
Ser—Glu—Lys—Tyr—Ser—Asn—Val—Ile—Phe—Leu—Glu—
Val—Asp—Val—Asp—Asp—Cys—Gln—Asp—Val—Ala—Ser—
Glu—Cys—Glu—Val—Lys—Cys—Met—Pro—Thr—Phe—Gln—
Phe—Phe—Lys—Lys—Gly—Gln—Lys—Val—Gly—Glu—Phe—
Ser—Gly—Ala—Asn—Lys—Glu—Lys—Leu—Glu—Ala—Thr—
100
Ile—Asn—Glu—Leu—Val'    [(C-terminal)]

3. The method of claim 1 wherein said human adult T cell leukemia-derived factor has been produced in *Escherichia coli*.

4. The method of claim 1, wherein said individual is in need of treatment for radiation damage caused by cancer therapy.

5. The method of claim 1, wherein said individual is in need of treatment for arteriosclerosis.

* * * * *